(12) United States Patent
Schroers et al.

(10) Patent No.: US 9,295,791 B2
(45) Date of Patent: Mar. 29, 2016

(54) DEVICE FOR DETECTING MOISTURE FOR AN ARRANGEMENT FOR MONITORING AN ACCESS TO A PATIENT

(71) Applicant: Fresenius Medical Care Deutschland GmbH, Bad Homburg (DE)

(72) Inventors: Alexander Schroers, Frankfurt (DE); John Heppe, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/936,979

(22) Filed: Jul. 8, 2013

(65) Prior Publication Data

US 2014/0012199 A1    Jan. 9, 2014

Related U.S. Application Data

(60) Provisional application No. 61/669,175, filed on Jul. 9, 2012.

(30) Foreign Application Priority Data

Jul. 9, 2012  (DE) .................. 10 2012 013 473

(51) Int. Cl.
  *A61M 5/50*     (2006.01)
  *G01M 3/18*     (2006.01)
  (Continued)

(52) U.S. Cl.
  CPC ............. *A61M 5/5086* (2013.01); *A61M 1/367* (2013.01); *G01M 3/16* (2013.01); *G01M 3/183* (2013.01); *G01M 3/186* (2013.01); *A61M 1/3653* (2013.01); *A61M 2205/15* (2013.01)

(58) Field of Classification Search
  CPC ............ A61M 5/5086; A61M 1/3653; A61M 1/3656; A61M 2205/15; A61M 1/367; G01M 3/186; G01M 3/16; G01M 3/183

USPC ............................................... 73/73; 604/111
See application file for complete search history.

(56) References Cited

U.S. PATENT DOCUMENTS

| | | | |
|---|---|---|---|
| 6,445,304 B1 | 9/2002 | Bandeian et al. | |
| 7,973,667 B2 * | 7/2011 | Crnkovich et al. | 340/604 |

(Continued)

FOREIGN PATENT DOCUMENTS

| | | | |
|---|---|---|---|
| DE | 10 2006 011313 B3 | 5/2007 | |
| EP | 0 491 971 A1 | 7/1992 | |

(Continued)

OTHER PUBLICATIONS

International Search Report, dated Sep. 16, 2013, from corresponding International Application No. PCT/EP2013/001947.

(Continued)

*Primary Examiner* — Hezron E Williams
*Assistant Examiner* — Marrit Eyassu
(74) *Attorney, Agent, or Firm* — Kenyon & Kenyon LLP

(57) ABSTRACT

A device for detecting moisture for an arrangement for monitoring an access to a patient for a system by which, via a flexible line, a liquid is fed to and/or out from the patient, for monitoring the vascular access in extra-corporeal blood treatment and for monitoring a central venous access in acute dialysis, an arrangement for monitoring an access to a patient, and a method of producing a device for detecting moisture for connection to a monitoring arrangement are described. The device for detecting moisture is characterized in that at least a part or portion of the device takes the form of a resilient attaching element having parts which fit round a flexible line and/or a system for connecting a flexible line. The attaching element, which is formed after the fashion of a clip, allows the device for detecting moisture to be attached quickly and securely to a flexible line.

17 Claims, 4 Drawing Sheets

(51) Int. Cl.
*G01M 3/16* (2006.01)
*A61M 1/36* (2006.01)

(56) References Cited

U.S. PATENT DOCUMENTS

| | | | | |
|---|---|---|---|---|
| 2002/0198483 | A1* | 12/2002 | Wariar et al. | 604/5.01 |
| 2005/0038325 | A1* | 2/2005 | Moll | 600/300 |
| 2009/0102180 | A1* | 4/2009 | Karling et al. | 285/20 |
| 2009/0284382 | A1* | 11/2009 | Hill | 340/604 |
| 2010/0228231 | A1 | 9/2010 | Weigel | |
| 2011/0217877 | A1* | 9/2011 | Linz | 439/625 |
| 2013/0165821 | A1* | 6/2013 | Freedman et al. | 601/2 |

FOREIGN PATENT DOCUMENTS

| | | |
|---|---|---|
| WO | 99/24145 | 5/1999 |
| WO | 99/24145 A1 | 5/1999 |
| WO | 2006/008866 | 1/2006 |
| WO | 2009/075592 A2 | 6/2009 |
| WO | 2011/116943 | 9/2011 |
| WO | 2011/116943 A1 | 9/2011 |

OTHER PUBLICATIONS

International Preliminary Report on Patentability (IPRP) dated Jan. 13, 2015 in PCT/EP2013/001947.

* cited by examiner

DEVICE FOR DETECTING MOISTURE FOR AN ARRANGEMENT FOR MONITORING AN ACCESS TO A PATIENT

CROSS REFERENCE TO RELATED APPLICATIONS

The present application claims priority to U.S. Provisional Patent Application Ser. No. 61/669,175, filed on Jul. 9, 2012, and Application No. DE 10 2012 013 473.8, filed in the Federal Republic of Germany on Jul. 9, 2012, each of which is expressly incorporated herein in its entirety by reference thereto.

FIELD OF INVENTION

The present invention relates to a device for detecting moisture for an arrangement for monitoring an access to a patient for a system by which, via a flexible line, a liquid is fed to a patient and/or a liquid is fed out from the patient, and in particular for monitoring the vascular access in extra-corporeal blood treatment and particularly for monitoring a central venous catheter in acute dialysis. The present invention also relates to an arrangement for monitoring an access to a patient which has a device for detecting moisture. The present invention also relates to a method of producing a device for detecting moisture for connection to an arrangement for monitoring a patient access.

BACKGROUND INFORMATION

In the field of medical engineering, there are various known systems with which, via a flexible line, liquids can be withdrawn from patients or liquids can be fed to patients. The access to the patients is generally gained in this case by means of a catheter for insertion in an organ of the body or by means of a needle for puncturing vessels. During the examination or treatment, it has to be ensured that proper access exists to the patient. It is therefore necessary for the patient access to be monitored.

Proper access to the patient is also a particular prerequisite for the pieces of extra-corporeal blood treatment apparatus which have an extra-corporeal blood circuit. The known pieces of extra-corporeal blood apparatus include for example pieces of dialysis apparatus and cell separators which require access to the patient's vascular system. In extra-corporeal blood treatment, blood is withdrawn from the patient along a flexible arterial line having an arterial puncturing needle and is fed back to the patient along a flexible venous line having a venous puncturing needle. In acute dialysis at intensive care stations, what is used as a patient access is a central venous catheter in the patient's neck.

In spite of regular monitoring of the vascular access by the hospital staff, there is, basically, a risk of the puncturing needle slipping out of the blood vessel unnoticed or of a connection in a flexible line becoming disconnected. There are various known arrangements of different forms for monitoring the vascular access. These known monitoring arrangements generally rely on the safety devices which are provided as standard in the pieces of blood treatment apparatus and which trigger an immediate shutoff of the extra-corporeal blood circuit if there is not a proper vascular access.

What is generally used to connect catheters and flexible lines for making a patient access is the Luer connecting system which is well known in the medical field and whose connecting parts comprise an inner and an outer cone which form tapers. This connecting system is referred to as a Luer lock connection when, to secure the connection, the inner and outer cones are supplemented with a screw thread. Although Luer lock connections provide a very high level of safety, it has been found in practice that the connecting parts, if not properly handled or if used too often or if there are faults in their material, may become disconnected or micro-cracks may develop in the material. U.S. Patent Application Publication No. 2010/0228231 therefore proposes securing the connecting parts of a Luer lock connecting system against unintentional disconnection with an additional means of fixing the connecting parts.

There are known arrangements for monitoring a vascular access which have a device for detecting moisture to enable the escape of blood to be detected at the site of the puncture. The known devices for detecting moisture which are used in the known monitoring arrangements for the patient access take the form of a pad to be applied to the site of the puncture. The pad consists of an absorbent material in which is embedded a moisture sensor. Devices for detecting moisture which comprise an absorbent material which is applied to the patient's skin are described in, for example, International Patent Publication No. WO 2006/008866, U.S. Patent Application Publication No. 2005/0038325 and U.S. Pat. No. 6,445,304. The characteristic feature of the known pads is that the moisture sensor is embedded in the absorbent material and the absorbent material is applied to the patient's skin.

International Patent Publication No. WO 99/24145 describes a device for detecting moisture which has a housing, able to be closed off with a lid, in which a moisture sensor is arranged. Provided in the housing are apertures for the needles and flexible lines to pass through. It is a disadvantage that the housing containing the moisture sensor is relatively expensive to produce in large numbers and is relatively difficult to handle in practice.

SUMMARY

An object underlying the present invention is to provide a device for detecting moisture which can be inexpensively produced in large numbers, which is easy to handle and which is very comfortable to be carried on the patient. A further object of the present invention is to provide an arrangement for monitoring an access to a patient which has a device for detecting moisture. It is also an object of the present invention to specify a method for the inexpensive production of a device for detecting moisture in large numbers.

The device according to the present invention for detecting moisture has a moisture sensor which takes the form of an electrically conductive structure. The moisture sensor of the device according to the present invention is connected to an arrangement for monitoring an access to a patient.

The device according to the present invention for detecting moisture is characterised in that at least a part or portion of the device takes the form of a resilient attaching element having parts which fit round a flexible line and/or a system for connecting flexible lines. The attaching element, which is formed after the fashion of a clip, allows the device for detecting moisture to be attached quickly and securely to a flexible line or to a system for connecting flexible lines. No additional attaching means are required for this purpose. It is not for example necessary for the device to be fixed to the flexible line, the connecting system or the patient's skin with adhesive tape. This simplifies the handling of the device.

In particular, the device according to the present invention can be attached in that region of the flexible line in which a connecting system, such as a Luer connecting system, for example, is situated. For this purpose, the device simply needs to be placed around the connecting system, thus enabling the point of connection to be monitored for leaks.

Whereas an additional means of securing a Luer connection which is described in U.S. Patent Application Publication No. 2010/0228231 is only able to prevent the connection from disconnecting, the device according to the present invention also enables a slow loss of blood to be detected, due for example to errors in making the connection in the flexible line or to faults in the material.

As well as this, it is also of advantage for the device according to the present invention to be easily able to be removed again from the flexible line after the treatment, which is important particularly when it is used to monitor a central venous catheter. The device can easily be detached from the flexible line even during the treatment. It is also possible for the device according to the present invention to be easily exchanged for a fresh one during the treatment.

The device according to the present invention may have one or more resilient attaching elements. The security of the fixing of the device to the flexible line can be increased by having a plurality of resilient attaching elements.

The device according to the present invention may be of different dimensions to allow it to be matched to the different dimensions of vascular accesses. It is crucial for the parts of the resilient attaching element to fit securely round the flexible line or the connecting system whatever the particular diameter thereof.

In a preferred exemplary embodiment, the device according to the present invention takes the form of a one-piece body which is resilient at least in a region or regions. The device preferably takes the form of an elongated body which can be fixed to the flexible tube or the connecting system for flexible tubes by having the latter snapped into it. A further preferred exemplary embodiment makes provision for the resilient attaching element to take the form of an annular body which is slit in the longitudinal direction. To insert the flexible line, the attaching element merely needs to be spread apart, the attaching element closing again under its own resilience. It is advantageous in this case for a disconnection to be able to occur at the device according to the present invention if there is a tensile stress on the electrical connecting line between the device for detecting moisture and the monitoring arrangement, which means that the patient access is not stressed in tension.

The handling of the device according to the present invention is further improved by giving the annular body, in the region of the slit, sections which are folded over in the outward direction on both sides. The folded over sections form a guide for the insertion of the flexible line.

The device according to the present invention preferably has a layer not permeable to liquid which is adjacent to the patient and situated on the outside and a layer absorbent of liquid which is remote from the patient and is situated on the inside. What is achieved in this way is that blood escaping at the point of the connection in the flexible line finds its way directly to the moisture sensor. It also prevents sweat from the patient's skin finding its way to the moisture sensor, thus preventing false alarms.

An exemplary embodiment of the present invention which is a particular preference makes provision for the absorbent material to be a textile material which has the electrically conductive structure. The electrically conductive structure may be embedded in the textile material or may be applied to the textile material.

The particular advantages of the device according to the present invention are, in particular, that the device can be produced easily in large numbers from a composite material comprising a preferably textile material having an electrically conductive structure and a thermally deformable substrate material, and that the composite item comprising the textile material and the substrate material is thermally deformed to form the resilient attaching elements. The devices according to the present invention can be inexpensively produced in large numbers by this method of production.

The electrically conductive structure of the moisture sensor preferably has at least one electrical conductor which is embedded in the textile material. The textile material is preferably a woven material having non-conductive warp filaments and non-conductive weft filaments and conductive warp filaments and conductive weft filaments, which are so arranged that the at least one conductor is formed. A woven material of this kind having an electrically conductive structure is described in detail in International Patent Publication No. WO 2011/116943.

The device according to the present invention preferably has connecting contacts to allow electrical contact to be made with the moisture sensor. It is however also possible for there to be run from the device according to the present invention an electrical connecting line which is connected to the monitoring arrangement.

A further preferred exemplary embodiment makes provision for the connecting contacts to be formed on the end-piece of an elongated sub-section of the device. This provides adequate physical separation between the connecting contacts and the moisture sensor. There is therefore no need for the region in which the electrical contact is made to be sterile, unlike the region in which the moisture sensor is situated. This is particularly advantageous when central venous catheters are being monitored.

In a particularly preferred exemplary embodiment, the device according to the present invention has two sub-sections which are spaced apart from one another and which take the form of resilient attaching elements. This exemplary embodiment allows the device according to the present invention to be fixed to the connecting parts of a flexible line which are in particular Luer lock connectors. The spacing between the two resilient attaching elements is of a size such that the connecting parts of the flexible line come to rest between the attaching elements.

A further preferred exemplary embodiment makes provision for a third resilient attaching element which is arranged between the first and second attaching elements. The third resilient attaching element is preferably longer than the first and second attaching elements. The device can be fixed to the connecting parts of the flexible line at the third resilient attaching element by enclosing the connecting parts in the third attaching element by snapping them into it. This increases still further the security with which the device according to the present invention is fixed to the flexible line.

The device according to the present invention comprising the composite item made up of a textile material and a deformable plastics material can be sterilised with no great technical cost or complication and can be made available in sterile form in suitable packaging as a disposable sensor The arrangement according to the present invention for monitoring an access to a patient, and in particular for monitoring a central venous catheter, has the device according to the present invention for detecting moisture, which is connected to the monitoring arrangement. The monitoring arrangement may trigger an audio and/or visual and/or tactile alarm if moisture is detected. It is also possible for a control signal to be generated for action in the control system controlling the system by which, via a flexible line, a liquid is fed to the patient and/or a liquid is fed out from the patient.

The arrangement according to the present invention for monitoring a patient access may form a separate unit or may be part of the system by which a liquid is fed to the patient and/or a liquid is fed out from the patient, and may in particular be part of the extra-corporeal blood treatment apparatus. If the monitoring arrangement according to the present invention is part of the blood treatment apparatus, the monitoring arrangement may make use of certain sub-assemblies or components which are present anyway in the blood treatment apparatus.

Exemplary embodiments of the device according to the present invention are explained in detail herein with reference to the accompanying drawings.

DETAILED DESCRIPTION

Figure 1:
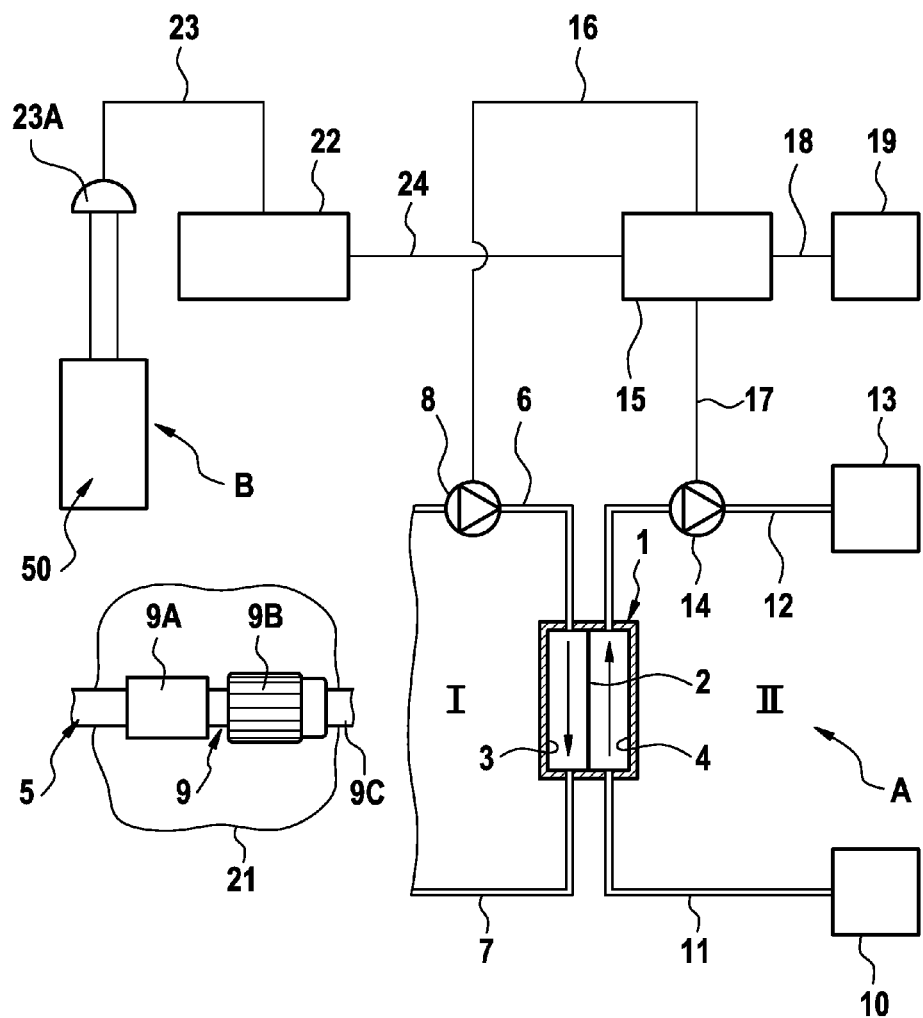
FIG. 1 shows the principal components of a blood treatment apparatus which has an arrangement for monitoring a vascular access.

FIG. 1 shows the principal components of a blood treatment apparatus, and in particular a haemodialysis apparatus A for acute dialysis, which has an arrangement B for monitoring a vascular access and in particular a vascular access which has a central venous catheter. The monitoring arrangement B is part of the haemodialysis apparatus A in the present exemplary embodiment. The dialysis apparatus will first be described by reference to FIG. 1.

The haemodialysis apparatus A has a dialyser 1 which is divided into a blood chamber 3 and a dialysis-fluid chamber 4 by a semi-permeable membrane 2. The vascular access to the patient is obtained by means of a central venous catheter 5 which is connected to the patient's neck. The central venous catheter 5 is part of the extra-corporeal blood circuit I, which is merely indicated and which includes the blood chamber 3 of the dialyser 1 and comprises the flexible lines 6, 7. A blood pump 8 is provided to pump the blood in the extra-corporeal circuit.

The dialysis-fluid circuit II of the dialysis apparatus A comprises a dialysis-fluid source 10 to which a dialysis-fluid infeed line 11, which runs to the inlet of the dialysis-fluid chamber 4 of the dialyser 1, is connected. Running off from the outlet of the dialysis-fluid chamber 4 of the dialyser 1 is a dialysis-fluid outfeed line 12 which runs to an outlet 13. A dialysis-fluid pump 14 is connected into the dialysis-fluid outfeed line 12.

Responsible for controlling the dialysis apparatus is a central control unit 15 which operates the blood and dialysis-fluid pumps 8, 14 via control lines 16, 17. The central control unit 15 is connected by a data line 18 to an alarm unit 19 which gives a visual and/or audio and/or tactile alarm if anything untoward happens.

In the present exemplary embodiment, the monitoring arrangement B, which is only shown schematically, is used to monitor a Luer lock connector 9 having parts 9A and 9B, for connecting the central venous catheter 5 to a flexible line 9C belonging to the extra-corporeal blood circuit I. The monitoring arrangement B has a device 50 for detecting moisture which is arranged at the point 21 of the connection to the flexible line. This moisture sensor 50 is only shown in schematic form in FIG. 1. As well as this, the monitoring arrangement B also has an analysing arrangement 22 which is electrically connected to the moisture sensor 50 by a connecting line 23. The connecting line 23 is connected to the moisture sensor 50 by an electrical connector 23A.

The analysing arrangement 22 is connected to the central control unit 15 of the dialysis apparatus A by a data line 24. In the event of blood escaping from the point of connection 21 to the flexible line and wetting the moisture sensor 50, the analysing arrangement 22 of the monitoring arrangement B generates a control signal which the central control unit 15 receives via the data line 24, the central control unit 15 then making an intervention in the blood treatment. The control unit 15 stops the blood pump 8 and generates an alarm signal so that the alarm unit 19 gives an audio and/or visual and/or tactile alarm.

In what follows, an exemplary embodiment of the device according to the present invention for detecting moisture will be described in detail by reference to FIGS. 2 to 6.

Figure 2:
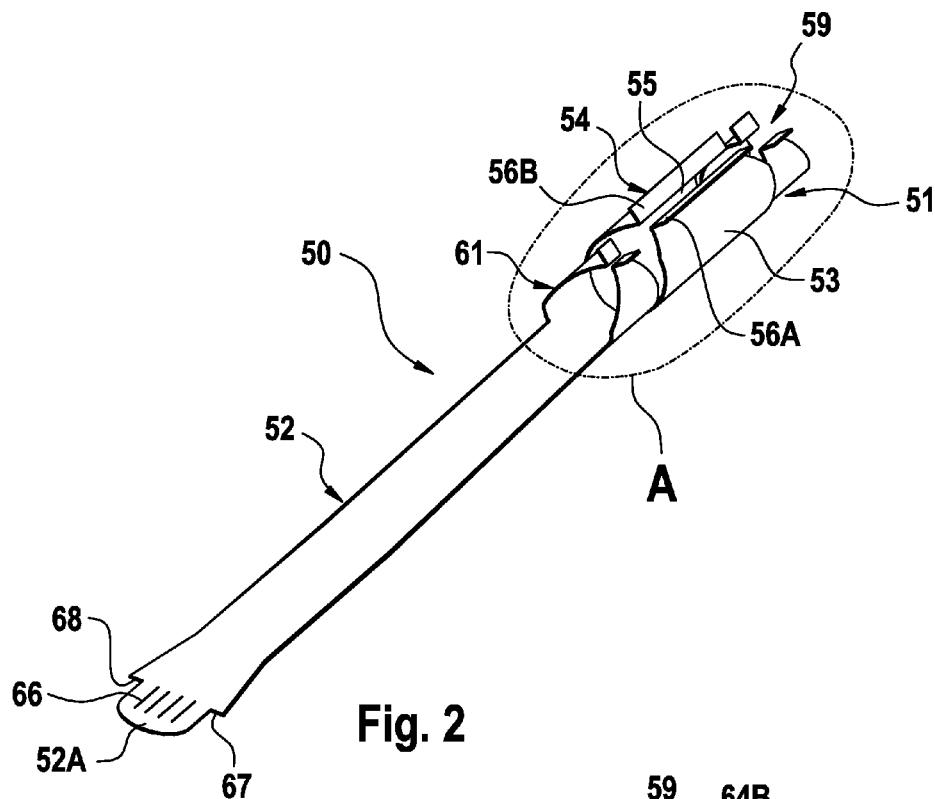
FIG. 2 is a perspective view of the device according to the present invention for detecting moisture.

FIG. 2 is a perspective view of an exemplary embodiment of the device 50 for detecting moisture. The device 50 is produced by the thermal deformation of a composite material comprising an absorbent textile material and a thermally deformable substrate material. The composite material and the method of production will be described in detail by reference to FIGS. 4 to 7.

The device 50 for detecting moisture takes the form of an elongated body which can be fixed to a flexible line (not shown) or a system for connecting a flexible line by having the latter snapped into it. The device is divided into a proximal portion 51 for fixing to a flexible line (not shown) or a system for connecting the flexible line and a distal portion 52 to which a connector for making the electrical connection to the monitoring arrangement is connected.

The central section 53 of the proximal portion 51 takes the form of a resilient attaching element 54 for the flexible line (not shown) or the system for connecting the flexible line. The central attaching element 54 is a sleeve-like body which is slit in the longitudinal direction. In the region of the slit 55, the central attaching element 54 has sections 56A, 56B which are folded over in the outward direction.

Figure 3:
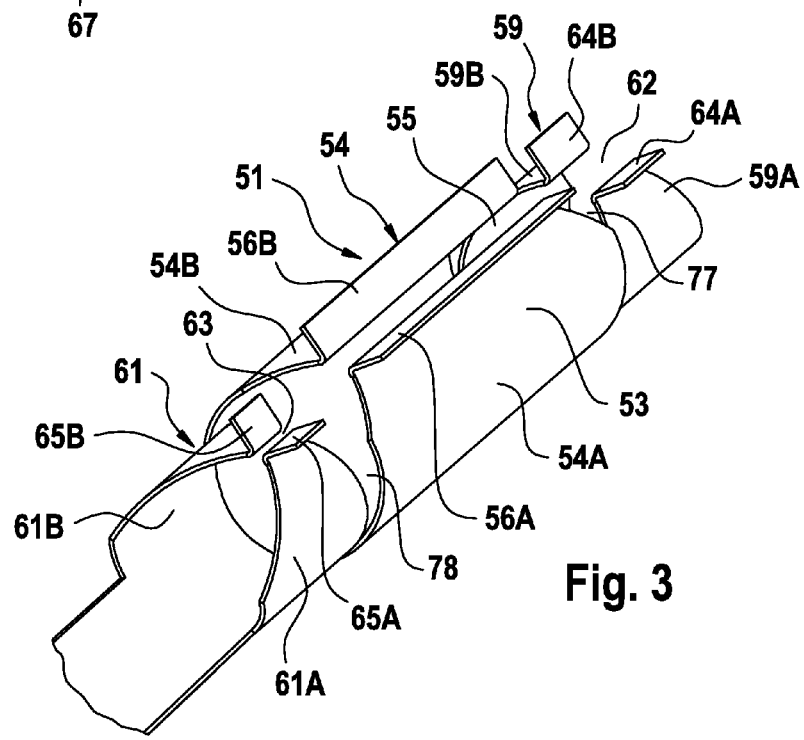
FIG. 3 is an enlarged view of detail A of FIG. 2.

FIG. 3 is an enlarged view of the proximal portion 51 of the device for detecting moisture, into which the flexible line (not shown), which comprises two sections which are connected together by means of connecting parts, is inserted. The connecting parts are the generally familiar Luer connecting parts 9A and 9B (FIG. 1).

The Luer lock parts for connecting the flexible line are enclosed by the two resilient parts 54A, 54B of the central attaching element 54, thus fixing the flexible line in place. The inside diameter of the central attaching element 54 therefore approximately corresponds to the outside diameter of the Luer lock connecting parts. The sections 56A, 56B of the central attaching element 54 which are folded over in the outward direction make it easier for the connecting parts to be inserted in that the two parts 54A, 54B of the central attaching element 54 can be spread apart by their inclined faces which are supported against the connecting parts. The length of the central attaching element 54 approximately corresponds to that of the two connecting parts.

Connecting up with the central attaching element 54 is a further, proximal, resilient attaching element 59 and a distal resilient attaching element 61. The proximal and distal attaching elements 59, 61 are sleeve-like bodies slit in the longitudinal direction which are of a smaller inside diameter than the central resilient attaching element 54. The proximal and distal attaching elements 59, 61 are both of the same inside diameter. The two attaching elements 59, 61 have parts 59A, 59B and 61A, 61B, respectively, which fit round the flexible line. In the region of their slits 62 and 63, respectively, the two attaching elements 59, 61 have sections 64A, 64B and 65A, 65B, respectively, which are folded over in the outward direction.

The proximal and distal attaching elements 59, 61 are separated from the central attaching element 54 by V-shaped incisions 77, 78. Because the inside diameter of the proximal and distal attaching elements 59, 61 corresponds to the outside diameter of the flexible line, the flexible line is additionally fixed in place by the proximal and distal attaching elements. In a similar way, the proximal and distal attaching elements act as stops for the parts connecting the flexible line because the inside diameter of the proximal and distal attaching elements 59, 61 is smaller than the outside diameter of the parts connecting the flexible line.

Should the device for detecting moisture be stressed in tension, it can easily be displaced in the longitudinal direction through an amount of play preset by the distance between the proximal and distal attaching elements, hardly any of the tractive force thus being transmitted to the central venous catheter. The function of a sort of "intended break point" is thereby performed.

The distal portion 52 of the device for detecting moisture is not thermally deformed. The distal portion 52 is a flat strip 79 to whose end-piece 52A the connector (not shown) of the connecting line running to the monitoring arrangement is connected.

The connecting contacts 66 of the moisture sensor of the device for detecting moisture are situated on the top face of the end-piece 52A. Formed on the end-piece 52A are lateral projections 67, 68 which form a stop for the connector (not shown). The moisture sensor will be described in what follows by reference to FIGS. 4 to 6.

Figure 4:
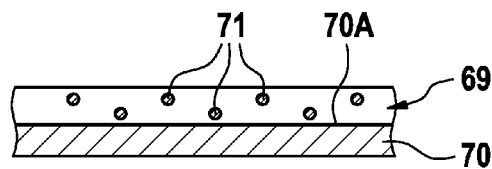
FIG. 4 is a section through the composite item comprising textile material and thermally deformable substrate material.

The device according to the present invention for detecting moisture is produced from a composite material comprising an absorbent textile material, and in particular a multi-ply woven material 69, and a thermally deformable substrate material 70. FIG. 4 is a section through the composite material. The bond between the woven material 69 and the substrate material 70 may for example be made by a layer of adhesive 70A. This does away with the need for lamination under high pressure. Excessively high pressure in any such lamination under pressure might in fact have an adverse effect on the structure of conductors in the textile material or might damage the conductors.

The multi-ply woven material comprises electrically conductive and electrically non-conductive warp and weft filaments (e.g., monofilaments, carbon fibres, silver coated polyamide yarns) which are merely schematically indicated in FIG. 4. The electrically conductive and electrically non-conductive warp and weft filaments 71 are so arranged that the woven material has a top ply, a centre ply and a bottom ply.

The electrically conductive structure of conductors forms the moisture sensor of the device for detecting moisture. A moisture sensor of this kind comprising warp and weft filaments is described in detail in International Patent Publication No. WO 2011/116943, which is hereby incorporated by reference.

Figures 5, 6:
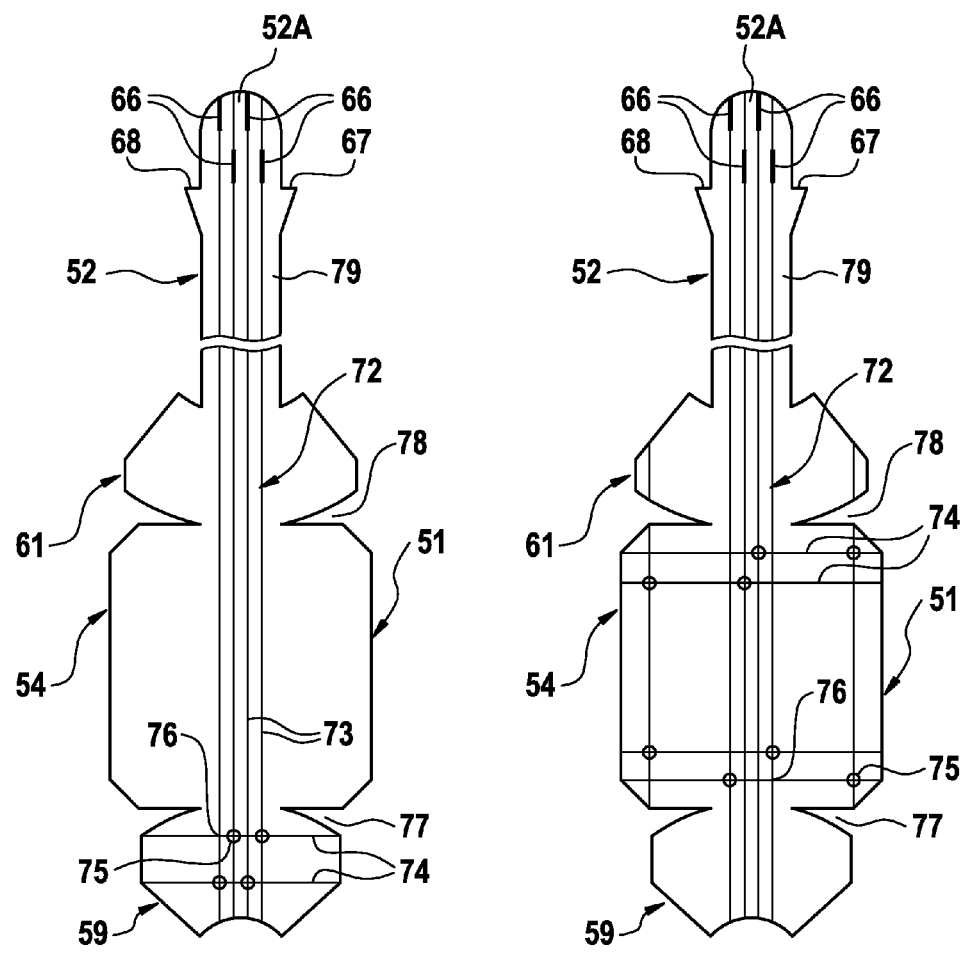
FIG. 5 shows a first exemplary embodiment of device according to the present invention before the deformation of the composite item comprising textile material and thermally deformable substrate material.
FIG. 6 shows a second exemplary embodiment of device according to the present invention before the deformation of the composite material.

FIGS. 5 and 6 are plan views of the composite material of the device for detecting moisture before the thermal deformation. The two exemplary embodiments shown in FIGS. 5 and 6 differ only in the layout of the moisture sensor. The reference numerals shown in FIGS. 1 and 2 have therefore been used to identify the individual parts of the device for detecting moisture.

The electrically conductive structure 72 of the moisture sensor comprises longitudinally extending conductors 73 and transversely extending conductors 74, which are in electrical contact at the intersections identified as 75 and which are isolated from one another electrically at the intersections identified as 76. At the ends of the longitudinally extending conductors 73 are the connecting contacts 66, which are staggered relative to one another in this exemplary embodiment.

The exemplary embodiment of moisture sensor shown in FIG. 6 is of greater sensitivity than that shown in FIG. 5, because the number of conductors is greater. As well as this, the moisture sensor shown in FIG. 6 is also sensitive in the edge regions of the central attaching element 54. The sensitivity of the moisture sensor shown in FIG. 5 is, however, adequate because the woven material is a material which is absorbent of liquid, such as blood, for example.

The V-shaped incisions 77, 78 between the resilient attaching elements make it easier for the flexible line to be inserted. Because the device for detecting moisture is fixed to the flexible line by having the latter snapped into it, the device can easily be pulled off the flexible line again. The respective diameters of the proximal attaching element 59, the distal attaching element 61 and the central attaching element 54 may be different. In particular, the diameter of the proximal and distal attaching elements 59, 61 may be smaller than that of the central attaching element 54. In the developed form shown in FIGS. 5 and 6, the V-shaped incisions 77, 78 are of radiuses which can be respectively matched to the diameter of the proximal and distal attaching elements 59, 61. The length of the strip-like portion 52 is of a size such that the connection to the moisture sensor is sufficiently far away from the sterile region.

The thermally deformable substrate material 70 is a material which, when acted on by temperature, maintains a permanent deformation and which is resilient after the deformation. The woven material 69 may for example be laminated to a stiff thermoplastic film as a substrate material. The temperature required for the thermal deformation depends on the substrate material. The temperature should be in a range which does not interfere with the properties, such for example as the hydrophilic properties, of the woven material and does not cause any damage to the points at which there is contact and isolation and so on.

Basically, it is also possible for only the textile material to be deformed plastically by suitable heat treatment to give a three-dimensional structure. Mechanical strength can be improved in this case by weaving thicker filaments into the woven material. However, the composite material comprising a thermoplastic film 70 and a woven material 69 has advantages in terms of mechanical properties such as elasticity and stiffness which are important to the handling and strength of the sensor. The thermoplastic film also performs the function of acting as a barrier against external moisture.

The substrate material 70 of plastics material may for example be a film of plastics material of a thickness of approx.

250 μm which can be produced from two polyester films of a thickness of approx. 125 μm, by laminating the films together with their sealing layers facing one another. The substrate material 70 is connected to the woven material 69 in a further lamination process. After being cut out to the outline shown in FIGS. 5 and 6, the composite material is thermally deformed in such a way that the three-dimensional shape shown in FIGS. 2 and 3 is obtained. The thermal deformation may for example be accomplished by the action of hot air or infrared radiation, as a result of which the sealing layer between the polyester films melts. The three-dimensional shape may for example be preset by a suitable core, which is of a cylindrical shape in the present exemplary embodiment. On the sealing layer of the polyester films melting, the composite material then assumes the form shown in FIGS. 2 and 3. It is however also possible for a thermoplastic film to be deformed.

Figure 7:
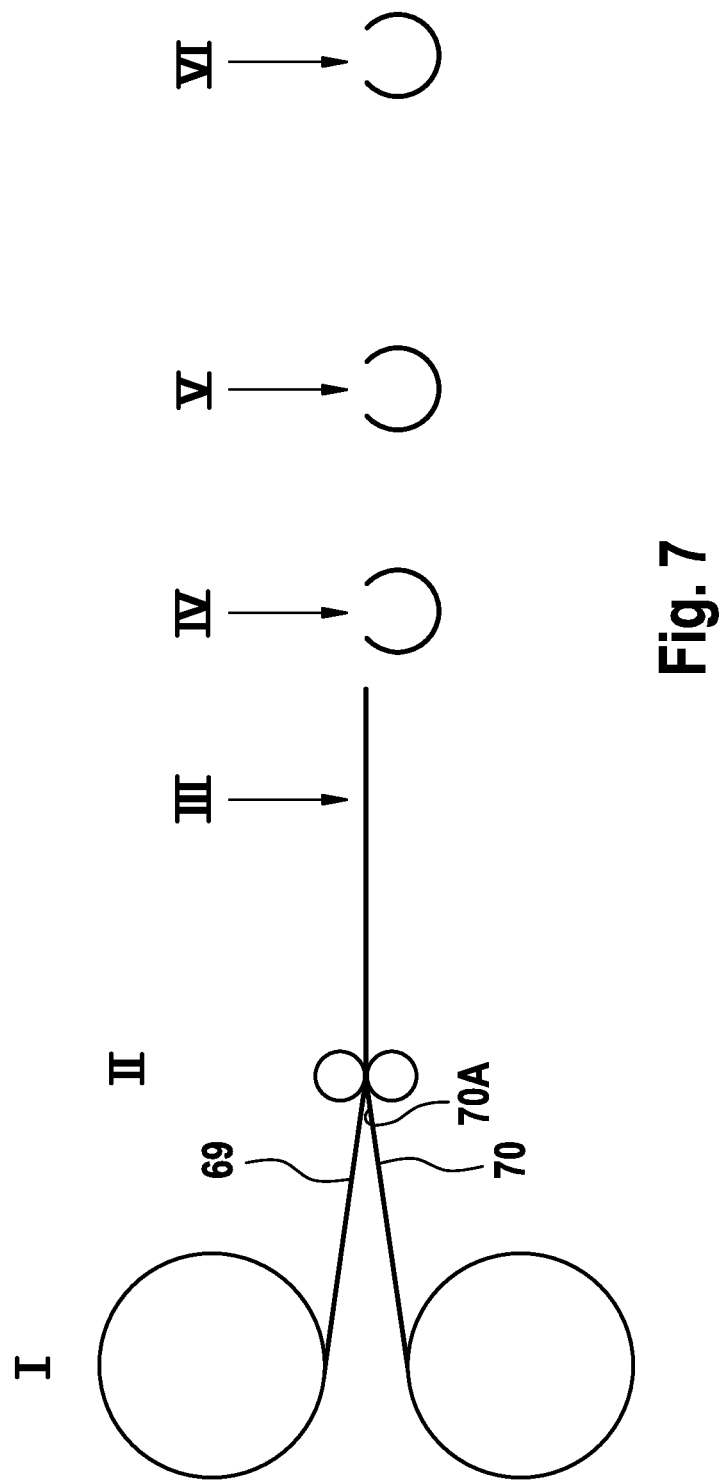
FIG. 7 is a schematic view to elucidate the steps in the process of producing the device according to the present invention.

FIG. 7 shows the individual steps in the process of producing the device according to the present invention for detecting moisture.

In a first step I in the production process, the woven material 69 and the substrate material 70 are produced in webs as materials in reel form. In a subsequent lamination process II, the woven material 69 and substrate material 70 are connected together by a layer of adhesive 70A. Then, in a further step III in the production process, the blanks shown in FIGS. 5 and 6 are separated from the web of material. This is followed by the step of the process IV in which the blanks which have been separated are thermally deformed. During the deformation, the developed blank which was cut out is fixed in the three-dimensional shape by tools. The forms of the tools forming the die and core determine the external outline of the sensor in this case. The die and core are heated during the thermal deformation and then cooled. This is followed by step V of the process, comprising the in-process control and release, and by step VI, the finishing and packaging.

The individual devices for detecting moisture can be protected against damage in non-deformable packaging. The devices may however equally well be packed in flexible packaging if inserted parts are used to protect them from being crushed.

What is claimed is:

1. A device for detecting moisture for an arrangement for monitoring an access to a patient for a system by which, via a flexible line, a liquid is fed at least one of to the patient or from the patient, or for monitoring a vascular access in extra-corporeal blood treatment, the device comprising:
   a moisture sensor including an electrically conductive structure comprising longitudinally extending conductors and transversely extending conductors; and
   at least one resilient attaching element situated in at least one portion of the device, the at least one resilient attaching element having parts which fit around at least one of the flexible line or a system for connecting the flexible line,
   wherein the at least one resilient attaching element has sections which are configured to spread apart and close under a resilience of the sections upon insertion of the flexible line or the system for connecting the flexible line,
   wherein the device is a one-piece body comprising the moisture sensor and the at least one resilient attaching element.

2. The device according to claim 1, wherein the device is an elongated body.

3. The device according to claim 1, wherein the at least one resilient attaching element is an annular body having a slit extending in a longitudinal direction of the device.

4. The device according to claim 3, wherein the annular body has, in a region of the slit, the sections, which sections are folded over in an outward direction away from the slit on opposing sides of the slit.

5. The device according to claim 3, wherein the slit extends from an interior of the at least one resilient attaching element to an exterior of the at least one resilient attaching element.

6. The device according to claim 1, wherein the device includes a layer not permeable to liquid which is adjacent to the patient, and a layer absorbent of liquid which is not adjacent to the patient.

7. The device according to claim 6, wherein the layer absorbent of liquid is a textile material which includes the electrically conductive structure.

8. The device according to claim 7, wherein the electrically conductive structure includes at least one electrical conductor embedded in the textile material.

9. The device according to claim 8, wherein the textile material is a woven material having non-conductive warp filaments and non-conductive weft filaments and conductive warp filaments and conductive weft filaments, which are so arranged to form the at least one electrical conductor.

10. The device according to claim 6, wherein the layer not permeable to liquid is a layer of resilient plastics material that is configured to be thermally deformed.

11. The device according to claim 1, wherein the device includes connecting contacts configured to allow electrical contact to be made with the moisture sensor.

12. The device according to claim 11, wherein the connecting contacts are formed on an end-piece of an elongated portion of the device.

13. The device according to claim 1, wherein the device includes two portions which are spaced apart from one another, a first portion including a first resilient attaching element and a second portion including a second resilient attaching element.

14. The device according to claim 13, wherein the device includes a third resilient attaching element arranged between the first and second resilient attaching elements.

15. The device according to claim 14, wherein the third resilient attaching element is of a greater length in a longitudinal direction of the device than the first and second resilient attaching elements.

16. An arrangement for monitoring an access to a patient for a system by which, via a flexible line, a liquid is fed at least one of to the patient or out from the patient, or for monitoring a vascular access in extra-corporeal blood treatment, the arrangement comprising:
   the device for detecting moisture according to claim 1.

17. A method of producing the device for detecting moisture according to claim 1, the method comprising:
   applying a textile material including an electrically conductive structure to a thermally deformable substrate material;
   cutting out, from the textile material and the substrate material, a composite item having a preset outline;
   thermally deforming the composite item including the textile material and the substrate material; and
   cooling the thermally deformed composite item including the textile material and the substrate material.

* * * * *